US012667372B2

(12) United States Patent
Barrus

(10) Patent No.: US 12,667,372 B2
(45) Date of Patent: Jun. 30, 2026

(54) FIXED ANGLE INSTRUMENT WITH ROUNDED LINKAGES

(71) Applicant: K2M, Inc., Leesburg, VA (US)

(72) Inventor: Michael Barrus, Redondo Beach, CA (US)

(73) Assignee: VB Spine US Opco LLC, Leesburg, VA (US)

( * ) Notice: Subject to any disclaimer, the term of this patent is extended or adjusted under 35 U.S.C. 154(b) by 801 days.

(21) Appl. No.: 17/724,868

(22) Filed: Apr. 20, 2022

(65) Prior Publication Data

US 2022/0338882 A1     Oct. 27, 2022

Related U.S. Application Data

(60) Provisional application No. 63/180,234, filed on Apr. 27, 2021.

(51) Int. Cl.
 *A61B 17/16* (2006.01)
 *A61B 17/34* (2006.01)
(52) U.S. Cl.
 CPC ...... *A61B 17/1622* (2013.01); *A61B 17/3496* (2013.01); *A61B 2017/3405* (2013.01)
(58) Field of Classification Search
 CPC ............ A61B 17/1622; A61B 17/3496; A61B 2017/3405
 See application file for complete search history.

(56) References Cited

U.S. PATENT DOCUMENTS

| | | | |
|---|---|---|---|
| 4,108,211 A | * | 8/1978 | Tanaka ................. A61B 1/0055 |
| | | | 138/120 |
| 4,442,908 A | | 4/1984 | Steenbock |
| 7,235,081 B2 | | 6/2007 | Errico et al. |
| 7,588,573 B2 | | 9/2009 | Berry |
| 8,998,924 B2 | | 4/2015 | Simpson et al. |
| 10,433,982 B2 | | 10/2019 | Willis et al. |
| 2010/0151161 A1 | * | 6/2010 | Da Rolo ................... F16C 1/04 |
| | | | 428/34.1 |
| 2014/0336675 A1 | * | 11/2014 | Menn ..................... A61B 17/10 |
| | | | 606/142 |
| 2018/0185037 A1 | | 7/2018 | Burley et al. |

* cited by examiner

*Primary Examiner* — Sameh R Boles
(74) *Attorney, Agent, or Firm* — Lerner David LLP

(57) ABSTRACT

A fixed angle instrument includes an elongate guide extending from a proximal end to a distal end, the guide having a proximal portion extending along a longitudinal axis and a distal portion extending transverse to the longitudinal axis. The instrument further includes a shaft disposed within the guide extending through the proximal portion of the guide along the longitudinal axis. The instrument further includes an intermediate element coupled to the shaft, the intermediate element having at least one bulbous link. The instrument further includes a distal element coupled to a distal end of the intermediate element.

11 Claims, 5 Drawing Sheets

SECTION A-A

FIXED ANGLE INSTRUMENT WITH ROUNDED LINKAGES

CROSS-REFERENCE TO RELATED APPLICATIONS

This application claims the benefit of the filing of U.S. Provisional Application No. 63/180,234 filed Apr. 27, 2021, the disclosure of which is hereby incorporated by reference herein in its entirety.

BACKGROUND OF THE INVENTION

Certain surgical procedures require the use of instruments that are specifically designed to avoid anatomical structures during their use. For instance, the anatomy of the spine is such that certain approaches for the insertion of spinal implants require the avoidance of bony structures such as the spinous processes or other structures such as nerves. Tools like awls and inserters thus have been created with bent or curved ends to facilitate the necessary avoidance. These instruments are typically referred to as fixed angle instruments and typically include complex structures that allow them to be utilized as intended.

Fixed angle instruments are challenging to design and manufacture and often do not function properly or as well as intended. Typically, the internal shaft of an angled instrument needs to be flexible to extend around obstacles and access hard-to-reach locations while still able to translate and/or rotate, potentially at the same time. To accomplish this, current designs include shafts made of braided wire or laser cut tubing to utilize flexibility. However, flexible shafts can be unreliable and imprecise. Other fixed angle instruments include rigid devices having an angled shaft or joint with a drill extending therefrom with only rotational capabilities.

Thus, further improvements in the field of instruments with an angled shaft are therefore desirable to address or improve upon at least the above-described shortcomings.

BRIEF SUMMARY OF THE INVENTION

The device described herein may be an instrument having at least a portion extending along a longitudinal axis and at least a portion extending transverse to the longitudinal axis. The instrument may include an outer rigid guide which extends along both the longitudinal axis and transverse to the same, having an angled portion therebetween forming a fixed angle between the two portions. The instrument may further include an inner shaft extending through the guide along the longitudinal axis, a distal element extending through the portion of the guide transverse to the longitudinal axis, and an intermediate element such as a linkage mechanism extending through the angled portion of the guide to couple the inner shaft to the distal element. The inner shaft, intermediate element, and distal element may be transitionally and/or rotationally fixed to each other such that these components may translate and/or rotate relative to the guide.

In certain embodiments, a fixed angle apparatus may include an elongate guide extending from a proximal end to a distal end, the guide having a proximal portion extending along a longitudinal axis and a distal portion extending transverse to the longitudinal axis, a shaft disposed within the guide extending through the proximal portion of the guide along the longitudinal axis, an intermediate element coupled to the shaft, the intermediate element having at least one bulbous link, and a distal element coupled to a distal end of the intermediate element. The distal portion of the guide may extend in a single direction transverse to the longitudinal axis and the intermediate element may be positioned between the proximal portion and the distal portion of the guide adapted to translate relative to the guide. The distal portion of the guide may define a curve and the intermediate element may be positioned within the distal portion adapted to translate relative to the distal portion. The shaft, the intermediate element, and the distal element may be adapted to translate and rotate together relative to the guide. The intermediate element may be a linkage mechanism including a plurality of links coupled in a sequence. Each link may have an elongate stem, a proximal hemispherical element with a flat surface facing a first direction, and a distal hemispherical element with a flat surface facing a second direction opposite the first direction. The proximal and distal hemispherical elements may define an aperture configured to receive a pin. The distal hemispherical element of a first link may be positioned to mate with a proximal hemispherical element of a second link such that the flat surfaces of the hemispherical elements abut one another and the apertures of the hemispherical elements align to receive the pin. The first link and the second link may be adapted to pivot about the pin with respect to each other.

A distal end of the shaft may include a hemispherical element having a flat surface positioned to mate with a proximal hemispherical element of a link, and a proximal end of the distal element may include a hemispherical element having a flat surface positioned to mate with a distal hemispherical element of a link. Each link may include a hollow receiving unit having an opening on a proximal face of the receiving unit and a protrusion extending distally from the receiving unit. The protrusion of a first link may be positioned to be received by the receiving unit of a second link. The receiving unit may define an aperture therethrough and the protrusion may define an aperture therethrough, and the protrusion of the first link may be configured to align with the receiving unit of the second link to receive a pin through the apertures of the protrusion and receiving unit. The first link may be configured to pivot with respect to the second link. A distal end of the shaft may include a protrusion adapted to be received and coupled to a receiving unit of a link by a pin. A proximal end of the distal element may include a receiving unit adapted to receive and be coupled to a protrusion of a link by a pin. The plurality of links may be translationally and rotationally fixed relative to each other. The distal element may be an awl. The distal element may be a drill. The distal element may be configured to be translated proximally relative to the guide such that a distal tip of the distal element is positioned proximal to the distal end of the guide.

In certain embodiments, a method of using a fixed angle instrument may include the steps of positioning a distal end of the fixed angle instrument in a target location, the fixed angle instrument having a linkage mechanism including at least one bulbous link disposed within a rigid guide; and applying a force to a proximal end of the fixed angle instrument, the force transferring from the proximal end of the fixed angle instrument to a distal end of a distal element of the instrument through the linkage mechanism such that at least a portion of the force is distributed from the at least one bulbous link to the rigid guide. The method may further include transitioning the distal element of the fixed angle instrument from a retracted configuration to a projecting configuration after the positioning step. The method may further include transitioning the distal element of fixed angle instrument from a projecting configuration to a retracted configuration after applying the force. The step of applying the force may include contacting the proximal end of the fixed angle instrument with a mallet or hammer. The distal element may be an awl and the step of applying the force may include puncturing a hole in the target location. The distal element may be an inserter and the step of applying the force may include inserting an implant into the target location.

DETAILED DESCRIPTION

As used herein, the term "proximal," when used in connection with a device or components of the device refers to the end of the device closer to the user (i.e., surgeon) when the device is being used as intended. On the other hand, the term "distal," when used in connection with a device or components of the device refers to the end of the device farther away from the user when the device is being used as intended. As used herein, the terms "about," "generally," "approximately," and "substantially" are intended to mean that slight deviations from absolute are included within the scope of the term so modified.

Figure 1:
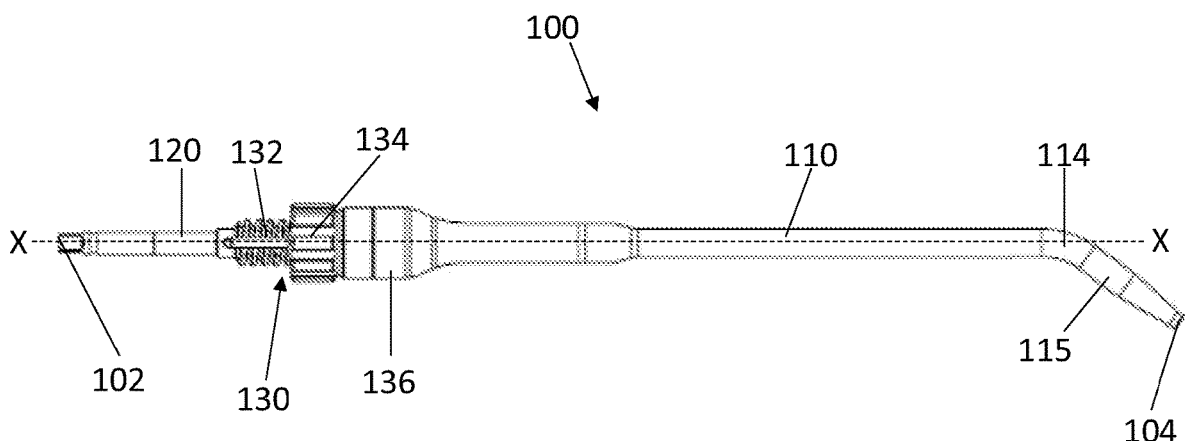
FIG. 1-3 are side, perspective and top views, respectively, of a fixed angle instrument according to an embodiment of the disclosure.
Figure 2:
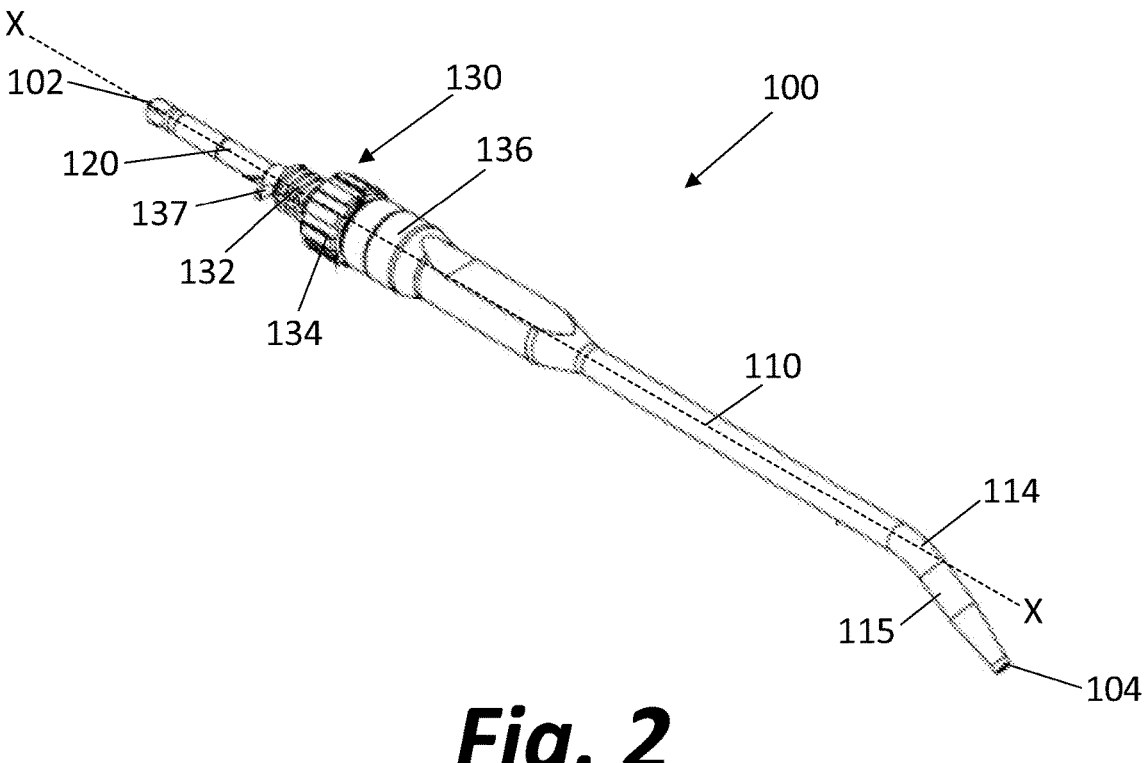

FIG. 1-5 illustrate a fixed angle instrument 100 according to an embodiment of the disclosure. Instrument 100 extends from a proximal end 102 to a distal end 104, including a guide 110, or outer shaft, formed by a hollow tube or cannula and an inner shaft 120 sized and shaped to extend through guide 110. A substantial portion of both guide 110 and inner shaft 120 extends along longitudinal axis X (see FIG. 4). As shown in FIGS. 1-2, guide 110 includes a rigid angled portion 114 and a distal portion 115 extending distally from angled portion 114 at an angle transverse or oblique to longitudinal axis X. It is contemplated that angled portion 114 may form an angle such that distal portion 115 extends at any angle between 0 and 180 degrees, relative to longitudinal axis X. In other words, distal portion 115 may form an obtuse angle with the portion of guide 110 extending along longitudinal axis X as shown in FIGS. 1-2, or the angle may alternatively be a right or acute angle, or distal portion 115 may extend generally in the opposite (e.g., proximal) direction forming a 180 degree angle. In certain embodiments, distal portion 115 may form an angle of approximately 45 degrees with longitudinal axis X. Distal portion 115 may extend in a single direction from longitudinal axis X as shown, or distal portion 115 and angled portion 114 may be one in the same such that together they form a steady curve, or any combination thereof. As such, angled portion 114 and/or distal portion 115 may have any radius of curvature suitable for the proper function of linkage mechanism 150 (discussed further below).

Figure 3:
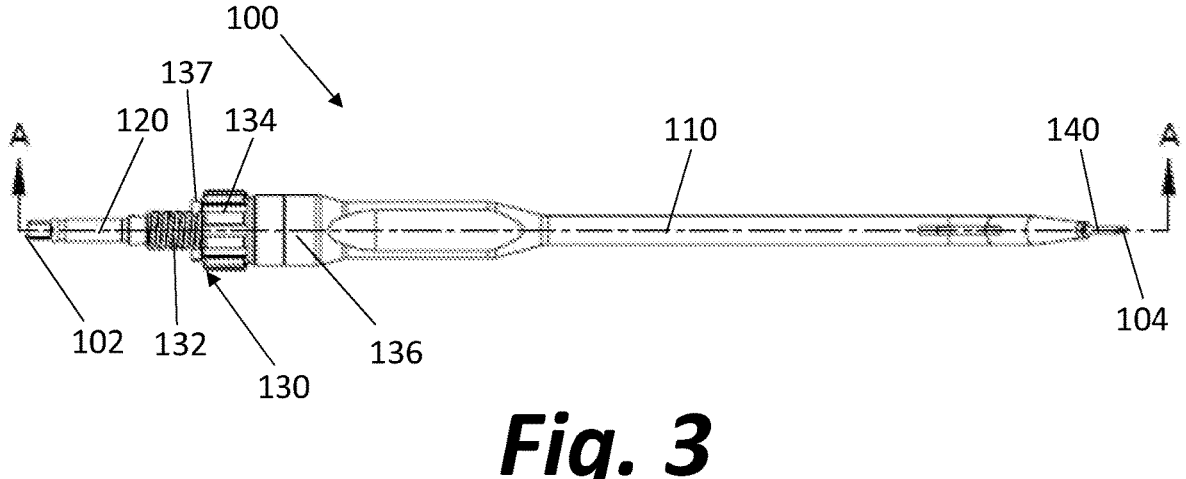

Inner shaft 120 is configured to translate proximally and distally relative to guide 110 via an actuation mechanism 130. Actuation mechanism 130 includes a threaded sleeve 132 disposed at least partially on a portion of inner shaft 120 which may protrude proximally from guide 110, and a generally cylindrical nut 134 having an aperture therethrough and an internal threading which corresponds to the threaded sleeve 132. As such, nut 134 is sized and shaped to be positioned over the inner shaft 120 and rotated along the threading of threaded sleeve 132. A proximal portion of guide 110 includes a flared portion 136 having a relatively larger diameter than the rest of guide 110. Nut 134 may be screwed onto threaded sleeve 132 until a distal face of nut 134 abuts a proximal face of flared portion 136, as shown in FIG. 3.

Inner shaft 120 includes an aperture configured to receive a pin 137. Nut 134 may be positioned over threaded sleeve 132 distally beyond the pin aperture, and pin 137 may be inserted into the aperture of inner shaft 120 such that nut 134 is generally sandwiched between pin 137 and flared portion 136 of guide 120. In such a position, nut 134 may be rotated relative to threaded sleeve 132 to translate inner shaft 120 relative to guide 110. For example, rotation of nut 134 (e.g., in a counter-clockwise direction) may cause proximal translation of nut 134 relative to threaded sleeve 132, and nut 134 may apply a proximally-directed force to pin 137 to translate inner shaft 120 in the proximal direction relative to guide 110. Further, rotation of nut 134 (e.g., in a clockwise direction) may cause distal translation of nut 134, at least until nut 134 abuts flared portion 136 of guide 120, and further rotation of nut 134 may cause distal translation of threaded sleeve 132 and thus inner shaft 120 relative to guide. A spring 138 is positioned within guide 110, a distal end of the spring 138 either fixed to guide 120 or abutting an interference element within guide 110, such as a central portion of guide 120 having a smaller diameter than flared portion 136 where spring 138 is disposed. Spring 138 may apply a biasing force upon inner shaft 120 in the proximal direction to maintain inner shaft 120 in a relatively proximal position until an opposing distal force is applied, which may improve the stability of inner shaft 120 and allow for a smooth transition between the retracted and projected configurations of the distal element, as described below in greater detail.

Figure 5:
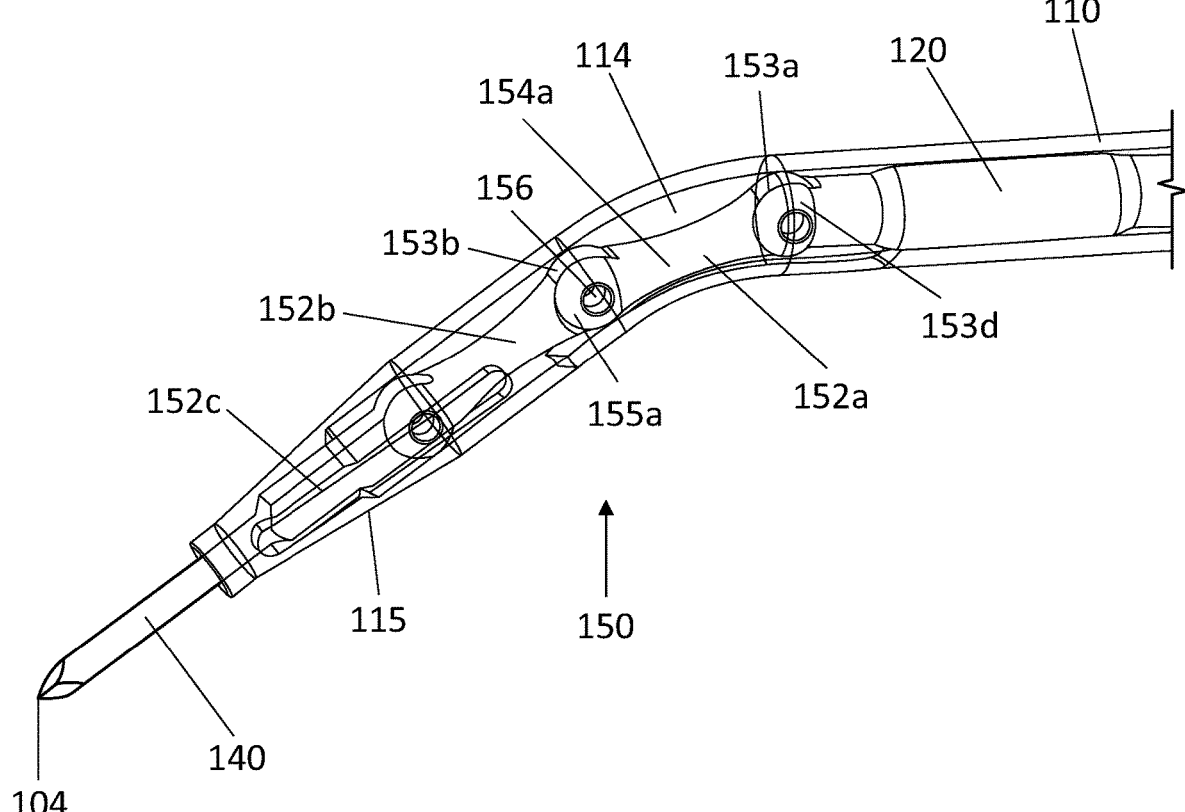
FIG. 5 a perspective view of a distal end of the fixed angle instrument of FIG. 1-3 with a transparent outer shaft.

A distal end of Inner shaft 120 is coupled to an intermediate element, such as a linkage mechanism 150, which is translationally fixed to inner shaft 120 and positioned to translate proximally and distally through angled portion 114. A distal end of linkage mechanism 150 may include or be coupled to a distal element, which may be a puncturing device such as an awl 140, coupled thereto for puncturing a hole in a target location. Awl 140 is translationally fixed to the distal end of linkage mechanism 150 such that translation of shaft 120 may cause corresponding translation of linkage mechanism 150 which may cause corresponding translation of awl 140. That is, proximal translation of shaft 120 may cause proximal translation of awl 140, and distal translation of shaft 120 may cause distal translation of awl 140. Awl 140 (or any distal element) may assume a retracted configuration in which awl 140 may be positioned such that a distal tip of awl 140 is disposed completely within guide 110 as shown in FIG. 1-2 (i.e., the distal tip of awl 140 is proximal to the distal tip of guide 110) to allow for safe transportation of instrument 100 to the desired target location, e.g., a region or portion of a patient's body. Maintaining instrument 100 in the retracted configuration may prevent any undesired contact between awl 140 and the surrounding environment, such as the body of the patient, to reduce or prevent unintended damage. Awl 140 may also assume a projecting configuration in which awl 140 protrudes from the distal end of guide 110 as shown in FIG. 5 to contact the targeted location and puncture a hole therein. As inner shaft 120 is translated proximally and distally by actuation mechanism 130, inner shaft 120 causes corresponding translational movement to linkage mechanism 150 and awl 140 to transition awl 140 between the retracted and projecting configurations.

Figure 4:
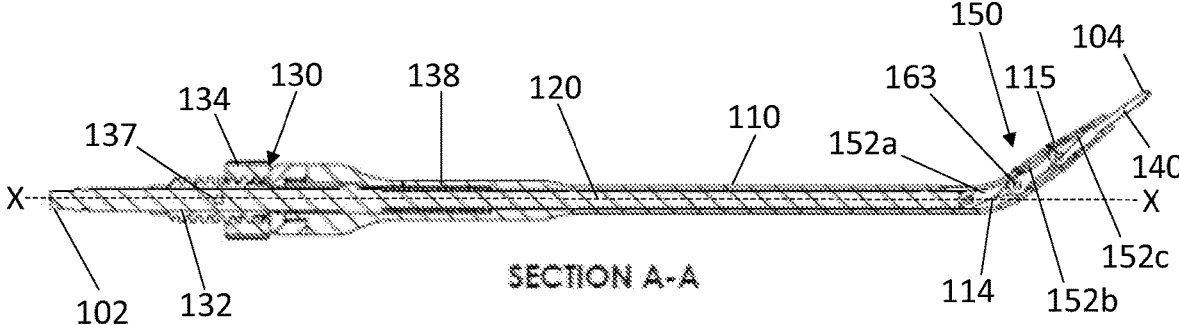
FIG. 4 is a cross-sectional view of the fixed angle instrument taken along line A-A in FIG. 3.

Linkage mechanism 150 may include one or a plurality of links. As shown in FIGS. 4-5, linkage mechanism 150 includes a first proximal link 152*a*, a second intermediate link 152*b*, and a third distal link 152*c*. Each link is generally elongate, extending from a proximal end to a distal end and having a generally hemispherical, or otherwise rounded or bulbous, element at each of the proximal and distal ends. For example, first link 152*a* shown in FIG. 5 includes a proximal hemispherical element 153*a* coupled to an elongate stem 154*a* extending distally from element 153*a* and a distal hemispherical element 155*a* coupled to the distal end of elongate stem 154*a*. Hemispherical elements 153*a*, 155*a* may face in opposite directions such that each element is configured to mate with the hemispherical element of an adjacent link. That is, proximal hemispherical element 153*a* of first link 152*a* is configured to mate with a distal hemispherical element 153*d* of shaft 120 and distal hemispherical element 155*a* of first link 152*a* is configured to mate with a proximal hemispherical element 153*b* of second intermediate link 152*b*. Each hemispherical element includes an aperture 156 extending therethrough. The hemispherical elements of adjacent links, such as elements 155*a* and 153*b*, may be mated such that a flat surface of each hemisphere abuts a flat surface of the other and the apertures 156 are aligned so as to receive a pin (shown as 163 in FIG. 4) to extend through both apertures. As such, adjacent links coupled at a joint of hemispherical elements may be adapted to articulate or pivot with respect to each other. The spherically shaped joints (due to the combination of two hemispherical elements) and the ability to articulate allow for a smooth and stable translation of linkage mechanism 150 through angled distal portion 114 of guide 110 to transition instrument 100 between the projecting configuration and the retracted configuration by translating awl 140 in and out of guide 110. The spherical joints may also stably absorb the force applied to each joint when awl 140 is positioned to abut a target location and the proximal end 102 of instrument 100 is impacted by an impacting tool, such as a mallet or hammer, to deliver a force from the awl 140 to the target location. The structure of instrument 100 may allow guide 110 to provide support to each of the spherical joints. That is, each joint may contact or abut the interior surface of the rigid guide 110 and the impact force may be dissipated from each of the spherical joints to guide 110, thus reducing the amount of force applied to the spherical joints, inner shaft 120 and awl 140, which may improve the effectiveness of instrument 100 and increase its longevity. It is contemplated that the puncturing device may be any similarly sized instrument used for any purpose, such as an awl, drill or screwdriver of any size, a knife with sharp edges for cutting, an inserter (e.g., for spinal implants), or the like as described below in greater detail. It is also contemplated that the instrument includes any number of links, including a single rounded link coupling the distal element to the shaft. Although the links are described herein as being rounded, the links may also have a bulbous or bulging shape, or the like, which may fulfill the intended purpose of the links as described above.

Figure 6:
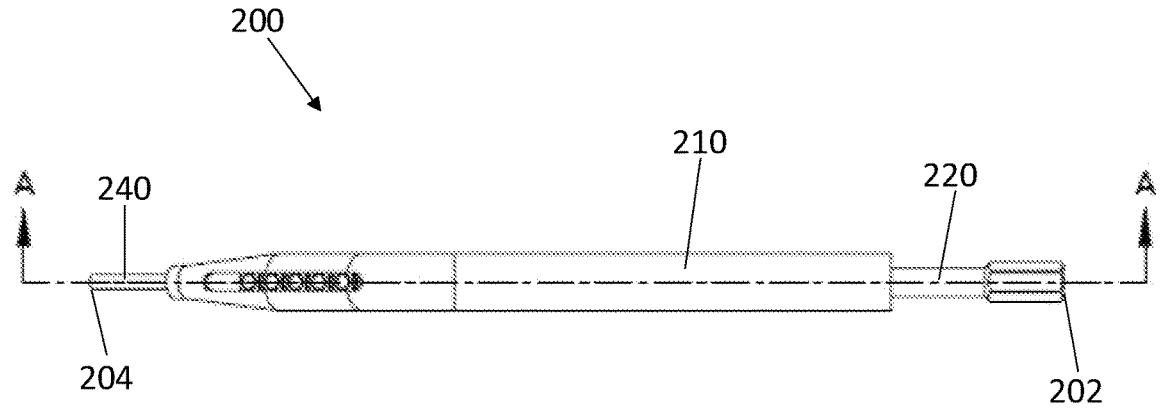
FIG. 6 is a top view of a fixed angle instrument according to another embodiment of the disclosure.
Figure 7:
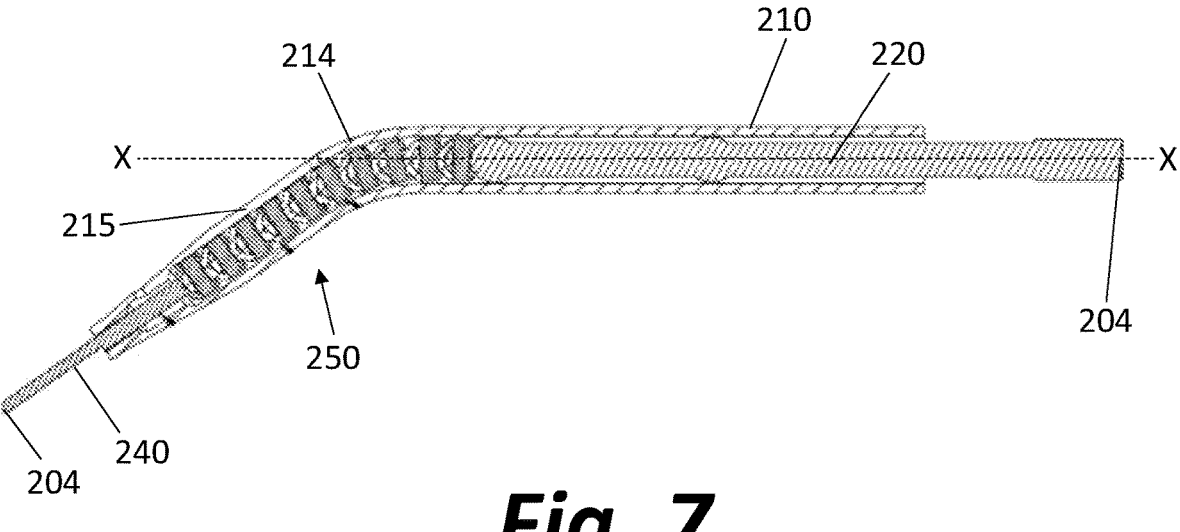
FIG. 7 is a cross-sectional view of the fixed angle instrument taken along line A-A in FIG. 6
Figure 8:
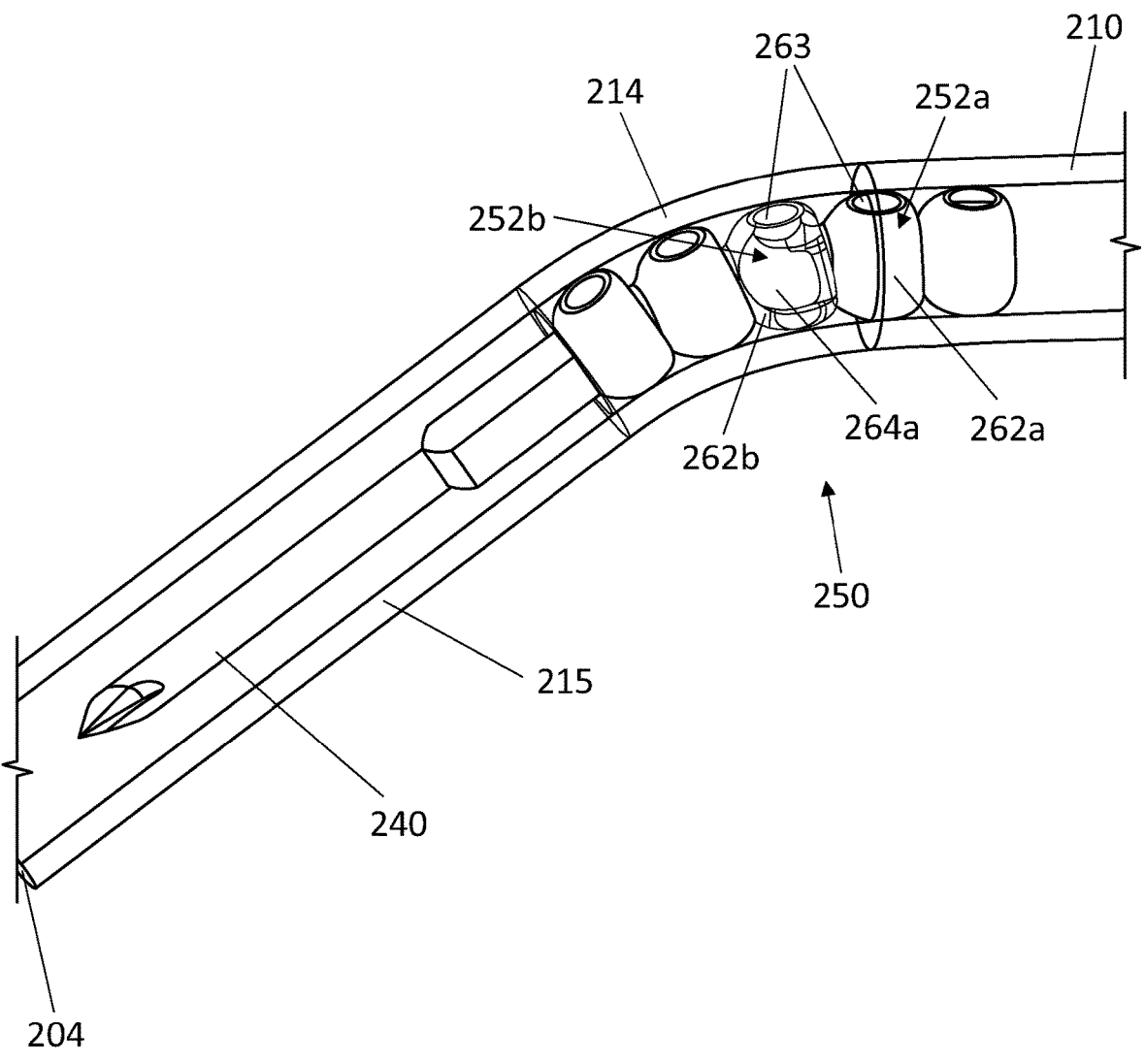
FIG. 8 is a perspective view of the fixed angle instrument of FIG. 6 with a transparent outer shaft.

FIGS. 6-8 illustrate a fixed angle instrument 200 according to another embodiment of the disclosure. It should be noted that like reference numerals labeled in instrument 200 refer to like elements of instrument 100, but within the 200-series of numerals. Instrument 200 extends from a proximal end 202 to a distal end 204. Instrument 200 includes a guide 210, or outer shaft, formed by a hollow tube or cannula and an inner shaft 220 sized and shaped to extend through guide 210. A substantial portion of both guide 210 and Inner shaft 220 extends along longitudinal axis X. Guide 210 includes a rigid angled portion 214 and a distal portion 215 extending distally from angled portion 214 at an angle transverse or oblique to longitudinal axis X. It is contemplated that angled portion 214 may form an angle such that distal portion 215 extends at any angle between 0 and 180 degrees relative to longitudinal axis X. In other words, distal portion 215 may form an obtuse angle with the portion of guide 210 extending along longitudinal axis X as shown in FIG. 7, or the angle may alternatively be a right or acute angle, or distal portion 215 may extend generally in the opposite (e.g., proximal) direction forming a 180 degree angle. In certain embodiments, distal portion 215 may form an angle of approximately 45 degrees with longitudinal axis X. Distal portion 215 may extend in a single direction from longitudinal axis X as shown, or distal portion 215 and angled portion 214 may be one in the same such that together they form a steady curve, or any combination thereof. As such, angled portion 214 and/or distal portion 215 may have any radius of curvature suitable for the proper function of linkage mechanism 250 (discussed further below). A proximal portion of inner shaft 220 extends proximally from guide 210, which may allow a user to grip or grasp inner shaft 220 with a hand or a tool to actuate inner shaft 220 relative to guide 210. Inner shaft 220 is configured to rotate relative to guide 210 and translate relative to guide 210.

A distal end of inner shaft 220 is coupled to an intermediate element, such as linkage mechanism 250, which is translationally fixed to inner shaft 220 and positioned to translate proximally and distally through angled portion 214. A distal end of linkage mechanism 250 may include or be coupled to a distal element such as drill 240, coupled thereto for drilling a hole in a target location. Drill 240 is translationally and rotationally fixed to linkage mechanism 250 such that translation and/or rotation of shaft 220 may cause corresponding translation and/or rotation of linkage mechanism 250 which may cause corresponding translation and/or rotation of drill 240. That is, as inner shaft 220 is translated proximally and distally by a user, inner shaft 220 causes corresponding translational movement to linkage mechanism 250 and drill 240. Substantially similar to awl 140 described above, drill 240 may assume the retracted configuration and the projection configuration. In the retracted configuration, drill 240 may be positioned such that a distal tip of drill 240 is disposed completely within guide 210 as shown in FIG. 8 (i.e., the distal tip of drill 240 is positioned proximal to the distal tip of guide 210) to allow for safe transportation of the instrument to the desired location, e.g., a region or portion of a patient's body. Maintaining instrument 200 in the retracted configuration may prevent any undesired contact between drill 240 and the surrounding environment, such as the body of the patient, to reduce or prevent unintended damage. In the projecting configuration, drill 240 may protrude from the distal end of guide 210 as shown in FIG. 7 to contact the targeted location and puncture a hole therein.

Linkage mechanism 250 includes a plurality of links as shown in FIGS. 7-8. It should be understood that each link may have substantially the same structure, with several links attached in sequence. For ease of illustration, the relationship between a pair of adjacent links is described herein, which may be applied to any other pair of adjacent links in linkage mechanism 250. FIG. 8 shows a first link 252a coupled to a second link 252b which is shown transparent to illustrate the connection between the two links. First link 252a includes a receiving unit 262a which has a rounded surface and may be generally spherical or generally cylindrical. Receiving unit 262a is generally hollow having a proximal-opening and an aperture sized and shaped to receive a pin 263. First link 252a further includes a protrusion 264a extending distally from receiving unit 262a, the protrusion 264a sized and shaped to fit within the receiving unit of an adjacent link, such as receiving unit 262b of second link 252b. Protrusion 264a also includes an aperture configured to receive pin 263. Protrusion 264a may be positioned within receiving unit 262b of second link 252b such that the aperture of protrusion 264a is aligned with the aperture of receiving unit 264b. Pin 263 may thereby extends through both apertures, the pin and apertures sized to stably couple first link 252a to second link 252b while allowing a small degree of pivoting with respect to each other. Each of the links of linkage mechanism 250 may be coupled to one another in the manner described above with respect to first and second links 252a, 252b. It is contemplated that instrument 200 may include any number of links, including a single link coupling the distal element to the shaft.

Similar to linkage mechanism 150 of instrument 100, adjacent links may be adapted to articulate or pivot with respect to one another. The articulation and the rounded shape of the links allow for a smooth and stable translation of linkage mechanism 250 through angled portion 214 of guide 210 to transition the instrument 200 between the projecting configuration and the retracted configuration by translating drill 240 in and out of guide 210. As noted above, the links may have any shape, such as bulbous, bulging, or the like, to achieve the intended purpose described herein. Further, the structure of linkage mechanism 250 allows for both translation and rotation of inner shaft 220, linkage mechanism 250, and drill 240 relative to guide 210. That is, inner shaft 220, linkage mechanism 250 and drill 240 are rotationally fixed in their connections to each other, and thus, the rotation of inner shaft 220 by a user causes the rotation of each of the links that form linkage mechanism 250, thereby ultimately causing the rotation of drill 240 relative to guide 210. Such an ability to translate and rotate allows a user to safely insert instrument 200 into a delicate or fragile location (e.g., a surgical site in the body of a patient) with drill 240 in the retracted configuration, access a hard-to-reach location using the angled feature of instrument 200, project drill 240 from instrument 200, and rotate drill 240 to drill, puncture, resect, etc. a desired location of the patient or any other destination.

In certain preferred embodiments of instruments 100, 200, each of the components may be made of stainless steel. In other aspects, components of the instruments may be made of metals such as titanium, carbon steel, aluminum, or the like. In further aspects, at least some of the components may be made of polymeric materials, such as plastics, polyethylene terephthalate (PET), polyether ether ketone (PEEK), or the like. In some embodiments, instruments 100, 200 may measure between approximately 10 inches and approximately 17 inches in the longitudinal direction from the proximal end to the distal end when the distal element is in the retracted configuration. In certain preferred embodiments, instruments 100, 200 may measure about 15.5 inches in the longitudinal direction. In certain preferred embodiments, the distal element may protrude approximately 18 millimeters from the distal tip of the guide when in the projecting configuration. In certain preferred embodiments, the angled portion of the guide may form an angle of approximately 35 degrees between the distal portion of the guide and the longitudinal axis along which the proximal portion of the guide extends.

As noted above, the instruments 100, 200 described herein are not limited to the uses for that which they are described. That is, instrument 100 is described with the distal element being a puncture device such as an awl to puncture a hole and instrument 200 is described with the distal element being a puncture device such as a drill. Instruments 100, 200 may alternatively include a sharp element such as a knife or a blade as the distal element in place of the puncture device. The sharp element may be used to perform cuts in parts of the body substantially blocked by bone or in hard-to-reach locations which may similarly require delivery of the instrument to the target location with the sharp element in the retracted configuration. In further examples, instruments 100, 200 may include a generally flat or blunt device (e.g., the impacting face of a hammer) as the distal element in place of the puncture device to apply high levels of consistent pressure or repetitive force in hard-to-reach locations.

In still further examples, instruments 100, 200 may include a device shaped to engage with and actuate a fastening unit, such as a screwdriver configured to drive a screw as the distal element. Instrument 200 may be particularly useful having the distal portion of the guide sized to fit a screwdriver which may be coupled to the linkage mechanism at its proximal end and releasably coupled (e.g., magnetically) to a screw at its distal end such that the screw may be completely disposed within the guide when the screwdriver is in the retracted configuration. In such examples, the instrument may be manipulated to transport the screw to the target location, the screw completely protected by the guide until the destination is reached, and subsequently projected from the guide via translation of the shaft, linkage mechanism and screwdriver. The screw may further be screwed into a target location via rotation of the shaft, linkage mechanism and screwdriver.

In other examples, instruments 100, 200 may include an inserter device configured to couple to an implant, such as a spinal implant, as the distal element. In such examples, the instrument may be used to deliver the implant to the surgical site, transporting the guide as near to the site as the distal end of the guide can reach, and subsequently translating and/or rotating the inserter device to manipulate the implant into the desired position, e.g., a spinal implant into an intervertebral disc space. Similar to the awl 140 described above, the instrument having an inserter device may be tapped or contacted by a mallet or hammer on the proximal end of the instrument to apply a force to the inserter device to insert the implant. In such an example, the linkage mechanism may similarly be particularly useful for distributing the applied force from the links to the surrounding rigid guide to improve the effectiveness and longevity of the instrument.

In other examples, instruments 100, 200 may include a suture needle as the distal element. A suture needle extending from the linkage mechanism may have a suture length coupled thereto and may be configured to be transported to a hard-to-reach location to deliver and apply a suture using the translational and/or rotational capabilities of the instrument. It is contemplated that the connection between the distal element (for any of the devices described herein) and the linkage mechanism may be modular such that the distal element may be detached from the instrument and replaced with any one of the devices described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixed angle apparatus, comprising: an elongate guide extending from a proximal end to a distal end, the guide having a proximal portion extending along a longitudinal axis and a distal portion extending transverse to the longitudinal axis; a shaft disposed within the guide extending through the proximal portion of the guide along the longitudinal axis; an intermediate element coupled to the shaft, the intermediate element having at least one bulbous link, each bulbous link configured to be pivotally coupled to an adjacent bulbous link about a rotational axis at a single joint; and a distal element coupled to a distal end of the intermediate element wherein the shaft, the intermediate element, and the distal element are adapted to rotate together relative to the elongate guide, wherein the intermediate element is a linkage mechanism including a plurality of bulbous links coupled in a sequence, wherein each link has an elongate stem, a proximal hemispherical element with a flat surface facing a first direction, and a distal hemispherical element with a flat surface facing a second direction opposite the first direction, wherein the proximal and distal hemispherical elements define an aperture configured to receive a pin.

2. The apparatus of claim 1, wherein the distal portion of the guide extends in a single direction transverse to the longitudinal axis and the intermediate element is positioned between the proximal portion and the distal portion of the guide adapted to translate relative to the guide.

3. The apparatus of claim 1, wherein the distal portion of the guide defines a curve and the intermediate element is positioned within the distal portion adapted to translate relative to the distal portion.

4. The apparatus of claim 1, wherein the shaft, the intermediate element, and the distal element are adapted to translate together relative to the elongate guide.

5. The apparatus of claim 1, wherein the distal hemispherical element of a first link is positioned to mate with a proximal hemispherical element of a second link such that the flat surfaces of the hemispherical elements abut one another and the apertures of the hemispherical elements align to receive the pin.

6. The apparatus of claim 5, wherein the first link and the second link are adapted to pivot about the pin with respect to each other.

7. The apparatus of claim 1, wherein a distal end of the shaft includes a hemispherical element having a flat surface positioned to mate with a proximal hemispherical element of a link, and a proximal end of the distal element includes a hemispherical element having a flat surface positioned to mate with a distal hemispherical element of a link.

8. The apparatus of claim 1, wherein the plurality of links are translationally and rotationally fixed relative to each other.

9. The apparatus of claim 1, wherein the distal element is an awl or a drill.

10. The apparatus of claim 1, wherein the distal element is configured to be translated proximally relative to the guide such that a distal tip of the distal element is positioned proximal to the distal end of the guide.

11. The apparatus of claim 1, wherein the rotational axis is transverse to the longitudinal axis.

* * * * *